United States Patent [19]

Bertness

[11] 4,253,272
[45] Mar. 3, 1981

[54] MOISTURE SENSING APPARATUS AND METHOD FOR AN AGRICULTURAL CHEMICAL APPLICATOR

[76] Inventor: Kevin I. Bertness, 2128 S. Riverside, Iowa City, Iowa 52240

[21] Appl. No.: 87,996

[22] Filed: Oct. 25, 1979

[51] Int. Cl.³ ............................................. A01C 23/00
[52] U.S. Cl. .................................... 47/1.5; 324/61 R
[58] Field of Search .................. 324/61 R; 47/1.5, 1.7

[56] References Cited

U.S. PATENT DOCUMENTS

| | | | |
|---|---|---|---|
| 3,227,951 | 1/1966 | Dykaar | 324/61 R |
| 3,857,095 | 12/1974 | Mitchie et al. | 324/61 R X |
| 3,936,735 | 2/1979 | de Bough | 324/61 R X |
| 3,950,698 | 4/1976 | Wochnowski | 324/61 R |
| 4,208,835 | 6/1980 | Roll et al. | 47/1.5 |

*Primary Examiner*—Robert E. Bagwill

*Attorney, Agent, or Firm*—Zarley, McKee, Thomte, Voorhees & Sease

[57] ABSTRACT

An apparatus and method for sensing the amount of liquid chemicals on the applicator roller of an agricultural chemical applicator are directed to an elongated sensor plate supported in generally parallel closely spaced relation to the roller and electrically insulated therefrom. Both the roller and sensor plate are electrically connected into an electrical circuit as opposite plates of a capacitor whereby the capacitance thereof increases with the amount of liquid chemicals on the roller. The electrical circuit interprets the capacitance as a measurement of the amount of liquid chemicals and compares that measurement to a predetermined value to provide an indication of whether additional liquid chemicals should be dispensed onto the roller.

14 Claims, 4 Drawing Figures

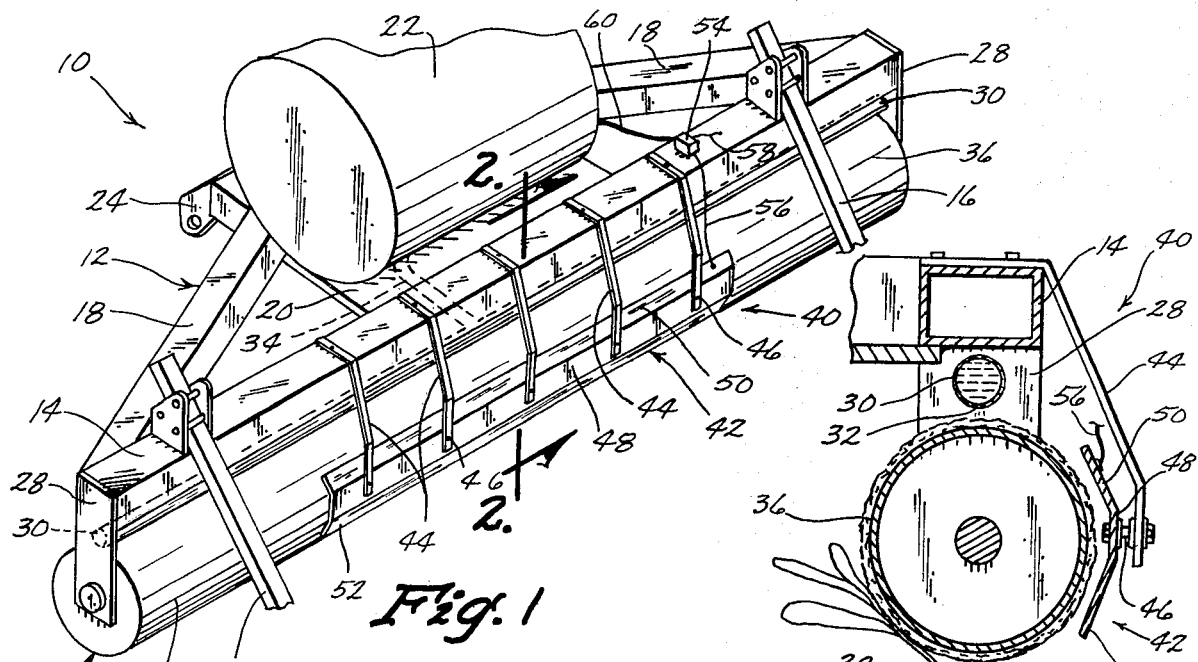
Fig. 1
Fig. 2
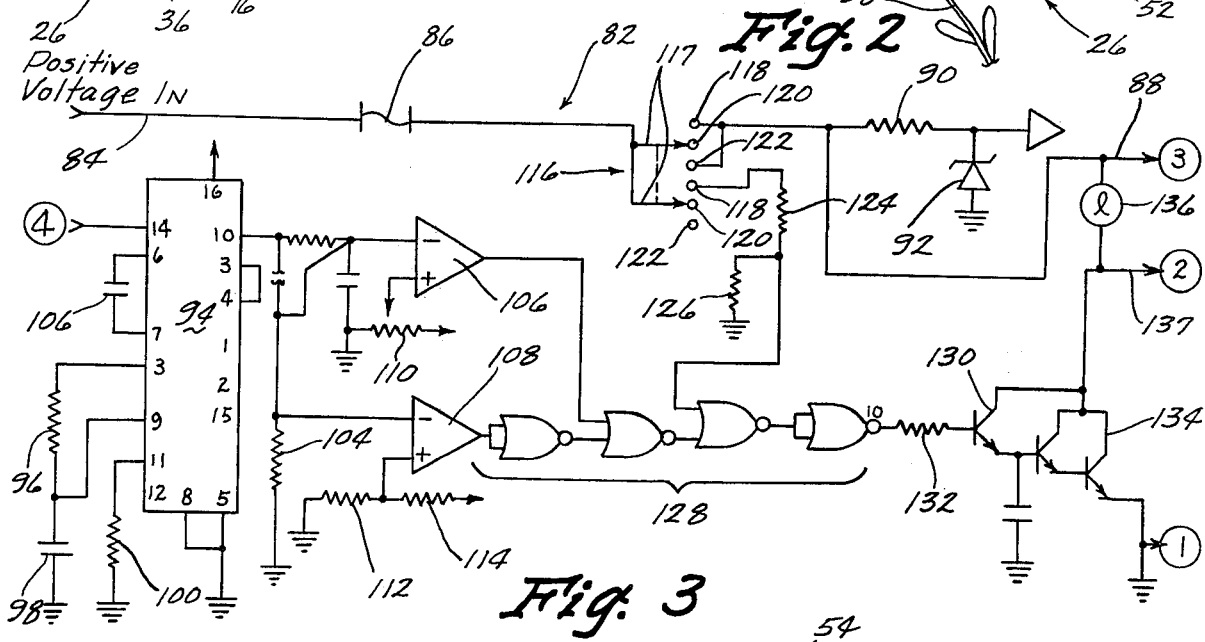
Fig. 3
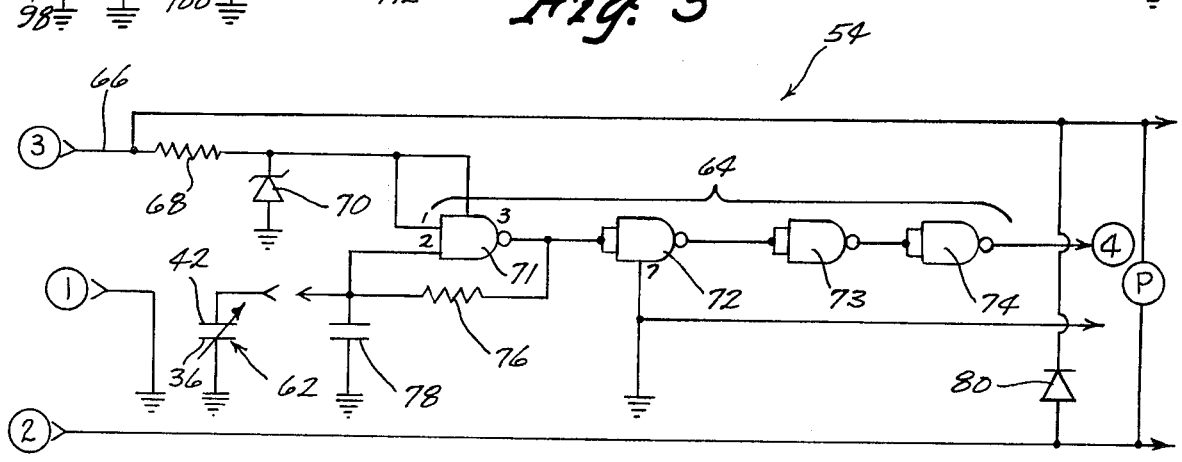
Fig. 4

MOISTURE SENSING APPARATUS AND METHOD FOR AN AGRICULTURAL CHEMICAL APPLICATOR

BACKGROUND OF THE INVENTION

The present invention is directed generally to a method and apparatus for sensing the amount of moisture on a surface and more particularly to a method and apparatus for sensing the amount of liquid chemicals on the applicator roller of an agricultural chemical applicator.

The application of liquid chemicals in the form of insecticides, for example, to crop plants is an essential part of successful modern farming. Because of the large quantities of chemicals applied, a significant financial savings can be achieved by maximizing the effectiveness and efficiency of the application process.

In one type of applicator, the liquid chemicals are dispensed onto an elongated roller adapted to contact crop plants directly as the applicator implement is moved across a field. A primary advantage of these applicators is that all of the liquid chemicals are applied to the leaves of the crop plants with none of the chemicals being scattered into the air or onto the bare ground between crop rows.

It is a problem, however, to adjust the dispensing rate of the chemicals onto the roller so as to maintain the roller surface moist with liquid chemicals while at the same time preventing an excessive buildup thereon which would result in waste. But in order to properly adjust the dispensing rate, it is essential to be able to sense the amount of liquid chemicals on the roller at a given time.

Accordingly, a primary object of the invention is to provide an improved apparatus and method for sensing the amount of moisture on a surface.

Another object is to provide a moisture sensing apparatus and method adapted to continuously sense the amount of moisture on a rotating roller.

Another object is to provide a moisture sensing apparatus and method which is adapted to prevent erroneous readings resulting from variations in the moisture level at axially spaced locations on the roller.

Another object is to provide a moisture sensing apparatus and method wherein a signal indicative of the moisture level on the roller is compared to a predetermined value corresponding to a desired moisture level for the roller, thereby providing an indication of whether additional moisture is to be dispensed onto the roller.

Another object is to provide a moisture sensing apparatus and method adapted for sensing the amount of liquid chemicals on the applicator roller of an agricultural chemical applicator.

Another object is to provide a moisture sensing apparatus and method which is simple in construction, durable in use and efficient in operation.

SUMMARY OF THE INVENTION

The moisture sensing apparatus of the present invention is particularly suitable for sensing the amount of liquid chemicals on the applicator roller of an agricultural chemical applicator. The moisture sensing apparatus includes an elongated sensor plate and means for supporting the plate in generally parallel closely spaced relation to the applicator roller. The sensor plate is electrically insulated from the roller however and both are connected into an electrical circuit as opposite plates of a capacitor whereby the capacitance thereof increases with the amount of moisture on the roller. The electrical circuit further interprets the capacitance of this capacitor as a measurement of the amount of liquid chemicals on the roller and compares this measurement to a predetermined value to provide an indication of whether additional liquid chemicals should be dispensed onto the roller. The elongated length of the sensor plate assures that the capacitance thereof is indicative of the moisture level on a significant portion of the roller. In the preferred embodiment, a pump and liquid chemical reservoir are transported with the applicator implement for dispensing additional chemicals onto the applicator roller as dictated by the results of said comparison. The moisture sensing apparatus and method of the present invention is operative to continuously sense the amount of liquid chemicals on the applicator roller and to actuate a pump for dispensing additional liquid chemicals onto the roller as needed to maintain a predetermined and uniform layer of liquid chemicals thereon.

The present invention further contemplates a method of sensing the amount of liquid chemicals on the surface of an agricultural chemical applicator roller, including the steps of supporting a sensor plate in generally parallel closely spaced relation to the roller and electrically insulating the plate from the roller, and electrically connecting the roller and sensor plate to an electrical circuit as opposite plates of a capacitor whereby the capacitance thereof increases with the amount of liquid chemicals on the roller.

BRIEF DESCRIPTION OF THE DRAWINGS

FIG. 1 is a partially fragmented perspective view of an agricultural chemical applicator including the moisture sensing apparatus of the invention;

FIG. 2 is an enlarged transverse sectional view taken along line 2—2 in FIG. 1;

FIG. 3 is a schematic electrical circuit diagram for the control head assembly of the invention; and FIG. 4 is a schematic electrical circuit diagram for the remote oscillator module of the invention.

DESCRIPTION OF THE PREFERRED EMBODIMENT

An agricultural chemical applicator 10 is shown in FIG. 1 as including a frame 12 having an elongated transversely extended tool bar 14 adapted to be supported by height-adjustable ground wheel support members 16. A pair of braces 18 converge forwardly from the tool bar 14 for supporting a platform 20 on which a liquid chemicals supply tank 22 is mounted. Suitable brackets 24 at the forward end of the platform provide for connection to the three-point hitch of an agricultural tractor whereby the applicator may be towed across a crop field.

Liquid chemicals are applied to the crop plants by an elongated applicator roller 26 rotatably supported by depending brackets 28 at each end of the tool bar 14. A liquid chemical dispensing tube 30 is mounted on the underside of the tool bar and includes a plurality of axially spaced openings 32 positioned above the roller 26. A supply tube 34 provides fluid communication between the supply tank 22 and dispensing tube 30. An electric pump, not shown, is disposed along the supply tube for pumping liquid chemicals to the dispensing tube at times.

Referring to FIG. 2, applicator roller 26 has a generally cylindrical surface 36 which is adapted to engage crop plants 38 as the applicator is advanced across a field. Liquid chemicals on the cylindrical surface 36 are then transferred directly to the crop leaves. The electric pump is operative to replenish the supply of liquid chemicals on the roller as dictated by the moisture sensing apparatus 40 of the present invention.

A moisture sensing apparatus 40 includes an elongated sensor plate 42 which is supported in generally parallel closely spaced relation to the applicator roller 26 by a plurality of spaced-apart support brackets 44. The brackets may be secured to the tool bar 14 and extended downwardly and rearwardly therefrom as shown in FIG. 2. Sensor plate 42 is connected to the lower end of the brackets 44 by a nylon bolt assembly 46 so as to electrically insulate the sensor plate from the implement frame 12 and thus the roller 26 as well.

In the preferred embodiment shown in the drawings, the sensor plate is constructed of 16 gauge mild steel and includes a generally narrow and flat central base portion 48 having integral flanges 50 and 52 inclined relative thereto so as to approximately follow the curvature of the roller surface 36.

A remote oscillator module 54 is shown in FIG. 1 mounted on the tool bar 14 and electrically connected to sensor plate 42 by a wire 56 and electrically grounded to the tool bar by a wire 58. In addition, the remote oscillator module 54 is connected by a four-wire harness to a control head assembly described hereinbelow. Gas-type connectors are used to insure good electrical contact and a strain relief is used on the control head for the wire harness and power input cord. Filled epoxy on the remote oscillator module 54 provides strain relief for that device.

Referring to the schematic circuit diagram of FIG. 4, the sensor plate 42 and roller surface 36 are connected into an electrical circuit as opposite plates of a capacitor 62 with the result that the capacitance thereof increases with the amount of moisture on the roller surface 36.

The remote oscillator module 54 consists of a CD4093BE complementary metal oxide semiconductor Schmidt-trigger quad two input NAND gate, hereinafter referred to as integrated circuit (I.C.) 64. A reference ground connection is applied to pin 7 of I.C. 64 and is supplied from the negative ground frame of a tractor to which the applicator 10 is connected. Positive tractor voltage (11–14 volts direct current) at 66 is dropped and regulated by means of resistor 68 and a zener diode 70. The reverse voltage breakdown characteristic of diode 70 is such that reverse voltage is maintained at a constant value (9 volts) provided sufficient sustaining current is maintained within the diode. Current through resistor 68 limits the zener diode 70 to prevent destructive current levels.

Integrated circuit 64 consists of four identical NAND gate section 71–74. Section 71 is used as the primary oscillator element. Feedback resistor 76, together with capacitor 78 and the sensor plate capacitor 62 determine the free-running oscillator frequency whose output is at pin 3 of NAND gate section 71. This frequency is a result of the charging time of the resistor 76, capacitor 78 and capacitor 62 connection, along with the internal characteristics of the NAND gate 71. In this circuit, a logical "0" is approximately equal to 0 volts, and a logical "1" is approximately equal to 9 volts.

Assuming the voltage at pin 3 is 0 volts, capacitor 78 and capacitor 62 are discharged and pin 2 of the NAND gate section 71 is then a logical "0". Pin 1 is constantly a logical "1". Therefore, the NAND function requires that pin 3 be a logical "1".

Capacitors 78 and 62 begin to charge through resistor 76. When a logical "1" Schmidt-trigger level is reached on pin 2, about 5.9 volts, the output at pin 3 goes from logical "1", 9 volts, to logical "0", 0 volts. Capacitors 78 and 62 then begin to discharge through resistor 76. When a logical "0" Schmidt-trigger level is reached on pin 2, about 3.9 volts, the output at pin 3 goes from logical "0" to logical "1". This cycling repeats indefinitely as long as power is supplied.

The sensor plate 42 and roller surface 36 of the chemical applicator 10 are connected as opposite plates of the capacitor 62. Greater moisture between the plate 42 and roller surface 36 cause greater capacitance due to the higher dielectric constant of water over air. This increases charging time and results in a lower frequency oscillator output at pin 3. Less moisture between the sensor plate 42 and roller surface 36 causes less capacitance due to air with a low dielectric constant occupying more space between the plate and the drum. This decreases charging time and results in a higher frequency oscillator output at pin 3.

The effect of capacitor 78 is to stabilize the effect of stray capacitance present in the system. These stray capacitances are of the order of 5–10 picofarads, and are variable. Their effect becomes negligible compared to the larger capacitor 78.

NAND gate sections 72, 73 and 74 are used to buffer the output of the oscillator 71. In complementary metal oxide semiconductor technology, unused inputs must be tied to valid logic levels in any case. Hence, NAND gate sections 72, 73 and 74 are cascaded for the sake of simplicity.

A zener diode 80 serves as transient protection for the main control circuit enclosed in the control head described hereinbelow in connection with FIG. 2. Diode 80 limits the collector-emitter voltage in the main driving transistor of the control head to a safe value, such as 0.7 volts above the supply voltage.

The remote oscillator module 54 is assembled on a single sided printed circuit board and is encased in an epoxy filled plastic encapsulation case for environmental integrity. It may be mounted on the tool bar 14 with a double sided foam tape.

FIG. 2 shows the circuit diagram for the control head 82 referred to above. Power to the control head is supplied from the 12-volt tractor battery at 84 through a 15 ampere fuse 86. Twelve volts is directed to the remote oscillator module wiring harness 60 at 88.

Positive tractor voltage, 11–14 volts direct current, is dropped and regulated by means of resistor 90 and zener diode 92. The reverse voltage breakdown of diode 92 is such that reverse voltage is maintained at a constant value, 9 volts, provided sufficient sustaining current is maintained within the diode. Current through resistor 90 limits the zener diode 92 to prevent destructive current levels.

Control head 82 includes a CD4046BE complementary metal oxide semiconductor micropower phase locked loop, referred to as integrated circuit (I.C.) 94. A phase locked loop consists of a phase comparator and a voltage controlled oscillator. The net effect of this circuit combination is to generate an output voltage proportional to the incoming signal frequency from the remote oscillator module 54.

A low pass filter is required to prevent locking to a signal harmonic. The pass band of this low pass filter is determined by resistor 96 and capacitor 98.

The center frequency of the voltage controlled oscillator and its range are controlled by resistor 100, and capacitor 102. Adjusting these components allows a full range voltage output, 0–9 volts, which is maximum sensitivity over the range of frequencies generated by the remote oscillator module 54.

Positive 9-volt power is supplied to pin 16 of I.C. 94 and ground is applied to pin 8 and pin 5, the inhibit operation control.

Tying pin 3 to pin 4 connects the output of the voltage controlled oscillator to the input of the phase comparator for closed-loop circuit operation.

The input from the remote oscillator module 54 is connected to pin 14 and pins 11, 2 and 15 are not used in this configuration.

The output at pin 10 is source follower and produces an output voltage when tied to ground through resistor 104 that is proportional to the incoming frequency from the remote oscillator module 54.

Integrated circuits 106 and 108 are configured as comparators. That is, when the voltage present at the negative input exceeds the voltage present at the positive input, the output goes low, logical "0". When the voltage present at the negative input is less than the voltage present at the positive input, the output goes high, logical "1".

Integrated circuit 106 compares the phase locked loop output voltage with the voltage from a variable resistor 110 which is mounted on a control panel, not shown, as the moisture level adjustment control.

Integrated circuit 108 compares the output of the phase locked loop 94 with the fixed voltage determined by resistors 112 and 114. This comparator detects when a problem has occurred with the remote oscillator 54 when the frequency becomes too high, for example. This condition would occur if the sensor wire 56 should become disconnected.

Resistor 96 and capacitor 102 act as a low pass filter time delay to prevent cycling due to moisture variation on the chemical applicator roller 26.

The control panel for circuit head 82 is also provided with a switch 116 including a pair of contact arms 117 selectively engageable with contacts 118, 120 and 122 to set the control head on manual (contacts 118), off (contacts 120) or automatic (contacts 122). Resistors 124 and 126 drop the logic level of the manual signal to a safe level, less than 9 volts.

An integrated circuit (I.C.) 128 includes four complementary metal oxide semiconductor NOR gates adapted to generate a logic signal for the pump driving circuit at 130 with the following implementation:

If switch 116 is set to manual, the pump is always on.
If switch 116 is set on off, the pump is always off.
If switch 116 is set to automatic:
and sensor wire 56 is broken, the pump is always off.
and sensor wire 56 is not broken, the pump is on or off depending on the moisture level and setting of the wetness control 110 on the control panel.

When the voltage at pin 10 of I.C. 128 is greater than approximately 2.1 volts, transistor 130 turns on. Base current is limited by resistor 132. When transistor 130 turns on, a second transistor 134 turns on and the driver line is brought low, causing the pump and a lamp 136 to turn on.

Capacitor 138 is used to prevent parasitic oscillation causing sporadic pump operation.

In operation, the agricultural chemical applicator 10 is transported to a crop field whereupon the ground wheel support members 16 are adjusted to properly set the height of the applicator roller 26 for rotatably engaging the crop plants as the implement traverses the field. The operator then refers to the control panel for the control head assembly 82 for setting the pump control switch 116 to either a manual position for constant pump operation or to the automatic position 122 wherein the pump is activated as dictated by the capacitance readings between the sensor plate 42 and roller surface 36.

A wetness control knob is also positioned on the control panel for adjusting the variable resistor 110 which acts as the source of a predetermined voltage for use in comparison with the voltage output of integrated circuit 94 by the integrated circuit comparator 106. Accordingly, the liquid chemical level on the roller 26 may be adjusted from a uniformly dampened surface to a surface wetted with a continuous fluid layer thereon. As flow is transferred to the crop plants during operation, the capacitance between the sensor plate 42 and roller surface 36 decreases whereupon the frequency generated by the integrated circuit 64 of the remote oscillator module 54 increases. The increased frequency input at pin 14 of the control head integrated circuit 94 causes a proportionately increased voltage to be applied to comparator 106. The resulting output from the comparison with the predetermined voltage of variable resistor 110 operates through integrated circuit 128 and transistors 130 and 134 to energize the pump circuit at 137 for replenishing the liquid chemical supply on the roller surface 36.

Whereas the invention has been shown and described in connection with an agricultural liquid chemical applicator, the present invention is advantageously suitable for various other applications wherein it is desired to sense the moisture level on a surface.

The method of the present invention for sensing moisture on a surface is believed to be apparent from the above disclosure and basically comprises supporting a sensor plate in closely spaced generally parallel relation to the applicator roller, electrically insulating the plate from the roller and electrically connecting the roller and plate to an electrical circuit as opposite plates of a capacitor whereby the capacitance thereof increases with the amount of liquid chemical on the roller. The method may also include interpreting the capacitance as a measurement of the amount of moisture on the roller and comparing that measurement to a predetermined value for an indication of whether additional liquid is to be applied to the roller surface.

Thus there has been shown and described a moisture sensing apparatus and method which accomplish at least all of the stated objects.

I claim:
1. An agricultural chemical applicator comprising,
a frame adapted for connection to a vehicle,
an elongated applicator roller rotatably carried on said frame, said roller having a generally cylindrical surface adapted to engage crop plants in response to movement of the frame by said vehicle,
a liquid chemical reservoir,
dispensing means in communication with said reservoir and operatively associated with said roller for dispensing liquid chemicals onto the surface thereof, an elongated sensor plate, support means for supporting said sensor plate on said frame in generally parallel closely spaced relation to said roller, said support means being adapted to electrically insulate said sensor plate from said surface, and an electrical circuit means wherein said sensor plate and roller surface are electrically connected as opposite plates of a capacitor, whereby the capacitance thereof increases with the amount of moisture on said surface, said electrical circuit including means for interpreting the capacitance of said capacitor as a measurement of the amount of moisture on said surface and means for comparing said measurement to a predetermined value.

2. The applicator of claim 1 wherein said means for interpreting said capacitance comprises a remote oscillator module adapted to generate a frequency which is a function of the capacitance of said capacitor and a control head assembly electrically connected to said remote oscillator module and adapted to generate a voltage proportional to said frequency.

3. The applicator of claim 2 further comprising a predetermined voltage source, said means for comparing said measurement to a predetermined value comprising a voltage comparator electrically connected to said control head assembly and to said predetermined voltage source for comparing the voltage generated by said control head assembly to the predetermined voltage, said comparator adapted to generate a signal indicative of the larger of said voltages.

4. The applicator of claim 3 further comprising a pump operatively associated with said dispensing means for directing chemicals from said reservoir through said dispensing means and onto said roller surface, and means for actuating said pump in response to said comparator signal.

5. The applicator of claim 4 wherein said predetermined voltage source is adjustable to selected settings for said predetermined voltage whereby the moisture level on said roller surface may be adjusted.

6. The applicator of claim 2 wherein said remote oscillator module comprises a complementary metal oxide semiconductor Schmidt-trigger quad two input NAND gate.

7. The applicator of claim 2 wherein said control head assembly comprises a complementary metal oxide semiconductor micropower phase locked loop.

8. The applicator of claim 1 wherein said sensor plate is of a length to overlie a substantial axial length of said roller.

9. The applicator of claim 8 wherein said sensor plate includes an elongated generally narrow and flat base member having at least one elongated flange inclined relative thereto so as to approximately conform to said cylindrical surface.

10. A method for sensing the amount of liquid chemicals on the applicator roller of an agricultural chemical applicator, comprising, providing an elongated sensor plate, supporting said sensor plate in closely spaced generally parallel relation to said roller, electrically insulating said sensor plate from said roller, providing an electrical circuit, electrically connecting said roller and sensor plate to said circuit as opposite plates of a capacitor whereby the capacitance thereof increases with the amount of liquid chemicals on said roller, interpreting said capacitance as a measurement of the amount of liquid chemicals on said roller, and comparing said measurement to a predetermined value.

11. The method of claim 10 further comprising adjusting said predetermined value to correspond to a desired amount of liquid chemicals on said roller.

12. The method of claim 11 further comprising dispensing additional liquid chemicals onto said roller in response to said comparing step, thereby to effect a closer comparison between said measurement and predetermined value.

13. The method of claim 10 wherein interpreting said capacitance comprises generating a frequency as a function of said capacitance and producing a voltage which is a function of said frequency.

14. The method of claim 13 wherein comparing said measurement comprises comparing said voltage to a predetermined voltage.

* * * * *